United States Patent
Shih et al.

(10) Patent No.: US 10,527,625 B2
(45) Date of Patent: Jan. 7, 2020

(54) CAPPED AND CONJUGATED QUANTUM DOTS

(71) Applicants: Wei-Heng Shih, Bryn Mawr, PA (US); Wan Y. Shih, Bryn Mawr, PA (US); Giang Au, Sicklerville, NJ (US); Ari D. Brooks, Cherry Hill, NJ (US); Vanlila K. Swami, Philadelphia, PA (US)

(72) Inventors: Wei-Heng Shih, Bryn Mawr, PA (US); Wan Y. Shih, Bryn Mawr, PA (US); Giang Au, Sicklerville, NJ (US); Ari D. Brooks, Cherry Hill, NJ (US); Vanlila K. Swami, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 290 days.

(21) Appl. No.: 15/202,710

(22) Filed: Jul. 6, 2016

(65) Prior Publication Data
US 2017/0212121 A1    Jul. 27, 2017

Related U.S. Application Data

(62) Division of application No. 14/119,996, filed as application No. PCT/US2012/039532 on May 25, 2012, now Pat. No. 9,417,240.

(60) Provisional application No. 61/491,006, filed on May 27, 2011.

(51) Int. Cl.
| | |
|---|---|
| *G01N 33/551* | (2006.01) |
| *G01N 33/574* | (2006.01) |
| *G01N 33/532* | (2006.01) |
| *G01N 33/58* | (2006.01) |
| *B82Y 15/00* | (2011.01) |
| *C07K 16/22* | (2006.01) |
| *C07K 16/30* | (2006.01) |
| *G01N 33/533* | (2006.01) |
| *B82Y 5/00* | (2011.01) |
| *B82Y 40/00* | (2011.01) |

(52) U.S. Cl.
CPC ........ *G01N 33/57488* (2013.01); *B82Y 15/00* (2013.01); *C07K 16/22* (2013.01); *C07K 16/30* (2013.01); *G01N 33/532* (2013.01); *G01N 33/533* (2013.01); *G01N 33/551* (2013.01); *G01N 33/574* (2013.01); *G01N 33/57484* (2013.01); *G01N 33/57492* (2013.01); *G01N 33/588* (2013.01); *B82Y 5/00* (2013.01); *B82Y 40/00* (2013.01); *G01N 2333/475* (2013.01); *G01N 2333/705* (2013.01); *G01N 2400/00* (2013.01); *G01N 2458/00* (2013.01); *Y10S 977/774* (2013.01); *Y10S 977/824* (2013.01); *Y10S 977/892* (2013.01); *Y10S 977/927* (2013.01)

(58) Field of Classification Search
None
See application file for complete search history.

(56) References Cited

U.S. PATENT DOCUMENTS

| | | |
|---|---|---|
| 6,167,297 A | 12/2000 | Benaron |
| 6,246,901 B1 | 6/2001 | Benaron |
| 6,365,124 B1 | 4/2002 | Babino et al. |
| 7,597,870 B2 | 10/2009 | Shih et al. |
| 7,790,473 B2 | 9/2010 | Barchi, Jr. et al. |
| 7,824,653 B2 | 11/2010 | Shih et al. |
| 7,912,653 B1 | 3/2011 | Scher et al. |
| 2004/0023415 A1 | 2/2004 | Sokolov et al. |
| 2007/0173718 A1 | 7/2007 | Richards-Kortum et al. |
| 2008/0107590 A1 | 5/2008 | Shih et al. |
| 2008/0199399 A1 | 8/2008 | Chen et al. |
| 2009/0065742 A1 | 3/2009 | Shih et al. |
| 2009/0068108 A1 | 3/2009 | Sokolov et al. |
| 2009/0269277 A1 | 10/2009 | Chang et al. |
| 2009/0286257 A1 | 11/2009 | Shih et al. |
| 2010/0210032 A1 | 8/2010 | Shih et al. |
| 2011/0001092 A1 | 1/2011 | Shih et al. |
| 2011/0003343 A1* | 1/2011 | Nikiforov .............. C07H 19/20 435/91.5 |
| 2011/0146766 A1* | 6/2011 | Nozik .................... B82Y 20/00 136/255 |

(Continued)

FOREIGN PATENT DOCUMENTS

| | | |
|---|---|---|
| EP | 1 487 343 B1 | 12/2008 |
| WO | WO2005093422 A2 | 10/2005 |

(Continued)

OTHER PUBLICATIONS

Shan, L., "Quantum Dot 800-Conjugated Anti-Tn IgM 2154F12A4 Murine Monoclonal Antibody," Aug. 21, 2009, pp. 1-4.

(Continued)

*Primary Examiner* — Christopher L Chin
(74) *Attorney, Agent, or Firm* — Mendelsohn Dunleavy, P.C.

(57) ABSTRACT

One or more aqueous, near infrared emitting, high yield, highly photoluminescent, stable quantum dots conjugated to one or more biomarkers specific moieties. The conjugated quantum dots have an enhanced detection sensitivity and selectivity and may be formed using a novel and efficient method for conjugating one or more biomarker specific moieties to the quantum dots. The invention is further directed to a method for using the conjugated quantum dots for cancer detection in the margin of excised tissue.

17 Claims, 4 Drawing Sheets

(56) References Cited

U.S. PATENT DOCUMENTS

2015/0038347 A1* 2/2015 Johnson ............... C12Q 1/6825
506/9

FOREIGN PATENT DOCUMENTS

| WO | WO2005102396 A2 | 11/2005 |
|---|---|---|
| WO | WO2006005065 A2 | 1/2006 |
| WO | WO2006107786 A3 | 10/2006 |
| WO | WO2008116079 A1 | 9/2008 |
| WO | WO2008140624 A2 | 11/2008 |
| WO | WO2009140757 A1 | 11/2009 |
| WO | WO2010019884 A1 | 2/2010 |
| WO | WO2010099543 A2 | 9/2010 |

OTHER PUBLICATIONS

Danussi, C., et al., "a Newly Generated Functional Antibody Identifies Tn Antigen as a Novel Determinant in the Cancer Cell-Lymphatic Endothelium Interaction," Glycobiology, Oct. 2009, vol. 19, No. 10, pp. 1056-1067.

Chan, W. C., et al., "Quantum Dot Bioconjugates for Ultrasensitive Nonisotopic Detection," American Association for the Advancement of Science, US, Sep. 25, 1998, vol. 281, pp. 2016-2018.

Roy, R., et al., "Glycodendrimers: Novel Glycotope Isosteres Unmasking Sugar Coding. Case Study with T-Antigen Markers from Breast Cancer MUC1 Glycoprotein," Review in Molecular Biotechnology, Elsevier, Amsterdam, NL, vol. 90, No. 3-4, May 1, 2002, pp. 291-309.

Wolcott, A., et al., "Silica-Coated CDTE Quantum Dots Functionalized with Thiols for Bioconjugation to IGG Proteins," Journal of Physical Chemistry. B, Materials, Surfaces, Interfaces and Biophysical, Washington, DC, US, vol. 110, No. 11, Jan. 1, 2006, pp. 5779-5789.

Zhang, Y., et al., "Self-assembly Multifunctional Nanocomposites with Fe304 Magnetic Core and CdSe/ZnS Quantum Dots Shell," Journal of Biomedical Material Research Part A, vol. 85A, No. 3, Jun. 1, 2008, pp. 840-846.

Yezhelyev, M. V., et al., "In Situ Molecular Profiling of Breast Cancer Biomarkers with Multicolor Quantum Dots," Advanced Materials, vol. 19, No. 20, Oct. 17, 2007, pp. 3146-3151.

Takeda, M., et al., "In vivo Single Molecular Imaging and Sentinel Node Navigation by Nanotechnology for Molecular Targeting Drug-Delivery Systems and Tailor-Made Medicine," Breast Cancer, vol. 15, No. 2, Mar. 4, 2008, pp. 145-152.

Zhang, H., et al., "Detection and Downregulation of Type I IGF Receptor Expression by Antibody-Conjugated Quantum Dots in Breast Cancer Cells," Breast Cancer Research and Treatment, Kluwer Academic Publishers, BO, vol. 114, No. 2, Apr. 17, 2008, pp. 277-285.

Almeida, D., et al., "Simple Silanization Routes of CdSe and CdTe Nanocrystals for Biological Applications," SPIE, vol. 7030, Aug. 21, 2008, pp. 703001-1-703001-8.

Zdobnova, T. A., et al., "Quantum Dots for Molecular Diagnostics of Tumors," Acta Nautrae, vol. 3, No. 1, Jan. 1, 2011, vol. 3, No. 1, Jan. 1, 2011, pp. 29-47.

Giang, H. T., et al., "Assessing Breast Cancer Margins Ex Vivo Using Aqueous Quantum-Dot-Molecular Probes," International Journal of Surgical Oncology, vol. 14, No. 6, Jan. 1, 2012, pp. 574-512.

European Examination Search Report; dated Mar. 27, 2015 for the corresponding EP Application No. EP12846223.1.

* cited by examiner

CAPPED AND CONJUGATED QUANTUM DOTS

RELATED APPLICATION DATA

This application is a divisional of U.S. patent application Ser. No. 14/119,996, filed Nov. 25, 2013, which claims priority to International Application No. PCT/US12/39532, filed May 25, 2012 and U.S. Provisional Application No. 61/491,006, filed May 27, 2011, the entire disclosure of which is hereby incorporated by reference as if set forth fully herein.

STATEMENT OF GOVERNMENT INTEREST

This invention was reduced to practice with Government support under Grant No. W81XWH-09-1-0701 awarded by the Department of Defense; the Government is therefore entitled to certain rights to this invention.

BACKGROUND OF THE INVENTION

Field of the Invention

The present invention relates to biomarker specific moieties conjugated quantum dots capable of highly sensitivity and selective biomarker detection.

Brief Description of the Prior Art

Breast cancer surgery relies on accurately assessing whether cancer cells are present in excised tissue to ensure complete tumor removal. As expected, the local cancer recurrence rate is higher for tissue margins testing positive for cancer cells within 3 mm of the margin surface (16%) in comparison to tissue margins that test negative (6%). Generally, re-excision is required if the tissue margin is found to contain cancer cells, which often results in additional cost, time, and pain to the patients. Estimates of the re-excision rate vary from 12% to as high as 60%. Morbidity and cancer recurrence rates were found to be much higher in patients who were re-excised. Consequently, it is highly desirable to cleanly remove a tumor with margins that test negative in a single surgical procedure.

Currently there is no reliable intraoperative margin assessment method. Conventional surgical procedures, such as preparation cytology (hereinafter "TPC") and frozen section analysis (hereinafter "FSA"), do not provide sufficiently reliable findings. TPC assumes that tumor cells will adhere to a clean glass surface, while other cells will not. The slides are then stained and reviewed by cytopathologists. FSA involves taking 1 cm×1 cm tissue samples from the walls of a surgical cavity and staining these samples with hematoxyline and eosin. The reliability of FSA and TPC are questionable due to histological artifacts. Currently, only a pathology exam is able to accurately assess the tissue margin.

VEGF antigen has little expression in normal cells, with the exception of wound sites that require the formation of additional blood vessels. Instead, VEGF is primarily expressed in cancerous cells. For example, VEGF is usually observed in breast cancer tissue, although the expression varies depending upon the histological grade of the tumor cells. The distribution of VEGF positive cells is not uniform. The strong expression is concentrated mainly along the edges of invasive tumors. Consequently, it is particularly well suited for detecting the presence of cancer cells in the margin of excised tissue. VEGF expression is correlated to the degree of differentiation. For invasive ductal carcinomas (IDC), VEGF is expressed in about 40% of cancer cells at stage I, about 75.6% of cancer cells at stage II and about 77.8% of cancer cells at stage III. As the cancer cells become more differentiated, e.g. mature, VEGF expression increases. For the non-invasive type of breast cancer, ductal carcinomas in situ (DCIS), VEGF is expressed in about 93% to about 100% of cancer cells.

The structure of TACAs, such as Tn antigen, are derived during neoplastic transformation changes within the glycosylation pathways. Tn antigens are only expression in cancer cells and are homogenously expressed throughout a tumor. There is no expression of Tn antigen in normal breast tissues. Furthermore anti-Tn antigen can be used to distinguish between benign and malignant cancer cells. Between about 60% to about 80% cancer cells express Tn antigen in DCIS and about 20% to about 50% of cancer cells express Tn antigen in lobular carcinoma in situ. Expression in IDC varies according tissue differentiation; at stage I it is expressed in about 70% cancer cells, at stage II it is expressed in about 90% to about 100% of cancer cells, and at stage III it is expressed in about 40% to about 60% of cancer cells. In contrast to VEGF antigens, which are only weakly expressed in invasive lobular carcinoma, Tn antigens are expressed in about 20% to about 70% of cancer cells in invasive lobular carcinoma.

Recently, quantum dots (hereinafter "QDs") have been proposed for use in various biomarker detection applications. WO/2008/140624, for example, discloses bioconjugated bifunctional nanoparticles for use in biomedical imaging applications. In some embodiments, nanoparticles are synthesized by a process that involves replacing a capping ligand such as mercaptopropionic acid (MPA) with another capping agent such as 3-mercaptopropyltrimethoxysilane (MPS). The nanoparticles may absorb light in the near-infrared optical region. To detect cancer cells, the nanoparticle may be conjugated with target moieties specific for a cancer biomarker, such as VEGF and EGFR. It is further contemplated that the nanoparticles may be used for intra-operative margin evaluation during surgery.

Danussi, Carla et. al. "A newly generated functional antibody identifies Tn antigen as a novel determinant in the cancer cell-lymphatic endothelium interaction," *Glycobiology*, 19(10), pps. 1056-1067, October 2009 discloses a study using anti-Tn IgM antibody conjugated QDs to determine the presence of metastatic cells in vivo and by analyzing excised tissue. The article teaches that Tn is expressed by 90% of human carcinomas and Tn antigen is proposed as a diagnostic and prognostic tumor biomarker for breast carcinoma.

Other references teach the synthesis of metal sulfide quantum dots for use in bioconjugation. For example, U.S. Patent Application No. 2009/0286257 discloses aqueous QDs for use in bioconjugation, such as CdPbS QDs, that emit light in the near infrared region, and U.S. Patent Application No. 2009/0065742 discloses aqueous QDs, such as MPS-replaced CdS and MPS-replaced ZnS QDs for use in bioconjugation.

There is a need to develop an improved biomarker specific conjugated QD that is reliable, accurate and capable of highly sensitive and selective biomarker detection as well as an improved method for quantum dot conjugation. Furthermore, there is a need to develop improved conjugated QDs capable of quickly and reliably assessing the margin of excised tissues in real time, allowing a surgeon to perform tissue excision and re-excision in a single surgical proce-

SUMMARY OF THE INVENTION

In a first aspect the invention is directed to quantum dots having a core selected from CdSe, CdPbS, and ZnSnS capped with MPA which has been at least partially replaced by MPS.

In a second aspect, the invention is directed to a conjugated quantum dot. The conjugated quantum dot comprises a quantum dot having a core, a thiol-functionalized capping agent and at least one biomarker specific moiety selected from anti-VEGF antibody and anti-Tn antigen antibody.

In a third aspect, the invention is directed to a method for conjugating one more biomarker specific moieties to one or more quantum dots involving the steps of: a) reacting a first conjugation linker with a capped quantum dot to form a reaction product; b) further reacting the reaction product of step a) with a second conjugation linker to form a second reaction product; and c) reacting the second reaction product of step b) with at least one biomarker specific moiety.

In a fourth aspect, the invention is directed to a method for cancer detection, wherein the method involves contacting near infrared emitting quantum dots with a tissue sample. Each of said quantum dots includes a core, at least one capping agent and at least one biomarker specific moiety conjugated to the quantum dot. The method further comprises the steps of removing unbound quantum dots and analyzing a near infrared emission from said tissue sample indicated of a presence or amount of bound quantum dots.

DETAILED DESCRIPTION OF THE PREFERRED EMBODIMENTS

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

For purposes of the present invention, the term "conjugation linker" as used herein refers to a molecule or compound to facilitate binding of one or more quantum dots to one or more biomarker specific moieties.

As used herein, the term "conjugated quantum dot" or "conjugated QD," refers to one or more quantum dots conjugated to one or more biomarker specific moieties.

As used herein, "moiety" refers to any biological agent, such as small molecules, peptides, antibodies, including monoclonal and recombinant antibodies as well as antibody fragments, nucleic acids, aptamers, epitopes or parts thereof.

As used herein, "biomarker specific moiety" refers to a moiety that binds specifically to a specific biomarker.

The present invention is directed to novel quantum dots, quantum dots conjugated to one or more biomarker specific moieties, a method for conjugating one or more biomarker specific moieties to one or more quantum dots and a method for using conjugated quantum dots for cancer detection. As an intraoperative diagnostic device, the invention is capable of reliably, rapidly, effectively and accurately identifying the presence and/or concentration of a biomarker. The detection method involves reacting a conjugated quantum dot with one or more biomarkers in the tissue, removing unreacted quantum dots and detected near infrared emissions from the bound quantum dots as an indicator of the presence of certain biomarkers. The one or more conjugated quantum dots (QDs) of the present invention may include: (1) one or more photoluminescent QDs each having a QD core with an exterior surface bound to at least one capping agent, and (2) one or more biomarker specific moieties bound to the one or more QDs.

1. The Quantum Dot

The aqueous QD of the present invention is a highly photoluminescent, aqueous nanocrystal that is stable and emits light in the near infrared spectrum. This ability to produce near infrared emissions, which is distinct from the auto-fluorescence produced by excised tissue, prevents the masking of QD emissions by tissue fluorescence. In an exemplary embodiment, the QD emits light in the range of about 700 nm to about 1100 nm, preferably about 700 nm to about 1000 nm, more preferably, about 775 nm to about 900 nm, more preferably, about 850 nm to about 900 nm and most preferably about 800 nm to about 875 nm, which is different than and can be distinguished from hemoglobin and water. In one embodiment, the QD has an excitation wavelength up to about 1100 nm. However, excitation wavelengths of about 300 nm about to about 1100 nm may be employed and more preferably, excitation wavelengths of 350 nm to 800 nm are employed.

Furthermore, unlike visible fluorescence which can only be detected within 1 mm of a tissue surface, near infrared emissions can be detected to a depth of several mm beneath the tissue surface. The near infrared QDs of the present invention may produce an emission spectrum that can be located up to at least about 10 mm below the tissue surface. Additionally, the QDs of the present invention have a high photoluminescent intensity to facilitate detection.

The composition of the QD core may be selected to generate a near-infrared emission at high photoluminescent intensity. In one embodiment, the QD core is composed of a metal sulfide, metal selenide or metal telluride. In one embodiment, the metal sulfide or metal selenide core may include two or more different metals. Preferably, the QD core may be composed of one or more non-toxic metals. Exemplary QD core compositions may include CdPbS, ZnSnS, CdSe, CdTe, CdS and ZnS.

For $Cd_xPb_{(1-x)}S$ QDs, x is preferably at least about 0.25, more preferably about 0.25 to about 0.85 and most preferably, about 0.4 to 0.8 to achieve high photoluminescence intensity, near infrared emission.

2. Capping Molecules

The QD core is capped with a thiol-functionalized capping agent, to stabilize the QD for a sufficient period of time to enable any desired application, including biomarker detection. Exemplary thiol functionalized capping agents include 4-aminothiophenol, mercaptosilanes such as 3-mercaptopropyltrimethoxysilane (MPS), and similar materials, as well as mercaptocarboxylic acids such as mercaptoacetic acid (MPA), mercaptopropionic acid, mercaptosuccinic acid, mercaptobenzoic acid, and mercaptoundecanoic acid. Any concentration of thiol-functionalized molecule may be employed, as long as it is within the solubility limit of the thiol-functionalized molecule in aqueous media. Additionally, any thiol-functionalized molecule with a charged group, preferably on the opposite end, may be used as a reactant during QD synthesis, as long as the thiol-functionalized molecule is water-soluble.

Photoluminescence intensity of the QD may be optimized by varying the capping molecule:cation:anion molar ratio. For capped CdPbS, CdS and ZnS QDs, the capping molecule:cation:anion molar ratio is preferably about 0.5:4:1 to about 8:4:1, more preferably from about 6:4:1 to about 12:6:1 and most preferably, about 1:4:1: to about 8:4:1. In one embodiment, the ratio of capping agent: metal: Se, Te or S is from about 2:1:1 to about 16:8:1. In another embodiment, the ratio of capping agent: metal: Se, Te or S is about 4:3:1 to about 8:5:1.

In an exemplary embodiment, the QD of the present invention is made by capping the QD with a first capping agent and then at least partially replacing the first capping agent with a second capping agent. It has been found that this method provides unexpectedly good stability to the QD. Also, the at least partial replacement can be used to include more desirable capping agents for particular applications, e.g. to enhance bonding efficiency with conjugation linkers and/or biomarker specific molecules.

In this method, at least some of the first capping molecules are replaced with at least some second capping molecules to enhance QD stability. The surface conditions of the QDs are modified by replacement of at least some of the first capping molecules with different second capping molecules, which produces a different surface chemistry than direct synthesis of the capped QDs with the first or second capping molecules alone or in a mixture. The second capping molecules bind to at least the surface of the QD and either partially or completely replace the first capping molecules.

The MPS replacement method includes the following two steps: (1) precipitation of the QDs with MPA, and (2) replacement of some or all of the MPA with MPS. First, MPA-capped QDs are produced directly in water. The obtained MPA-capped QD suspension was quenched and stored in a refrigerator. Preferably, the sample is allowed to reach equilibrium before carrying out the second step of the MPS replacement method. In the second step, a basic MPS solution was added and mixed thoroughly with the MPA-capped QDs whereby at least some of the MPA capping molecules are replaced by MPS capping molecules. Different amounts of MPS may be used to prepare samples with different MPS:metal:sulfur/selenide/telluride ratios, with the amount of MPS preferably being sufficient to provide ratios of MPS:metal:sulfur/selenide of from about 0.125:4:1 to about 12:4:1, more preferably, from about 0.5:4:1 to about 10:4:1 and, most preferably, from about 0.5:4:1 to about 8:4:1.

In one embodiment, the molar ratio of MPS:QD used in the replacement reaction, particularly QD containing sulfur, is preferably about 0.125:1 to about 16:1, more preferably, about 0.2:1 to about 8:1 and most preferably, about 0.5:1 to about 4:1. In one embodiment, the molar ratio of MPS:QD used in the replacement reaction, particularly QD containing selenium or tellurium, is preferably about 0.125:1 to about 16:1, more preferably, about 0.5:1 to about 8:1 and most preferably, about 0.1:1 to about 4:1. In another embodiment, the molar ratio of MPS used to replace MPA:QD is about 0.5 to about 4.

In one embodiment, MPS replaced MPA capping molecules may be bound to the QD by: (1) precipitating the QD with MPA and (2) replacing of some or all of the MPA with MPS. During synthesis, MPA-capped QDs are produced directly in solution. The QD core solution and MPA are mixed and stirred in deionized water, and the pH of the mixture is adjusted to about 12. A sodium sulfide or sodium selenide solution may be added to precipitate the nanoparticles. Subsequently, excess cations and/or anions may be added to adjust the MPA:cation:anion molar ratio in order to enhance emission. The synthesized MPA-capped QD suspension may be subsequently quenched to about 0° C. and stored in a refrigerator at about 4° C.

After the sample reaches equilibrium, MPS may be used to replace MPA. During this process, the MPA-capped QDs may be filtered or spun, using a microcentrifuge, to remove any unused MPA molecules and other ions in the suspension. An aqueous solution of MPS is made and, if necessary, the pH of the MPS solution may be adjusted to about 12 by adding a base. The basic MPS solution may be added to the MPA-capped QD suspension and reacted with the MPA-capped QD to replace some or all of the MPA with MPS. The amount of MPS solution employed can be used to adjust the degree of replacement of MPA with MPS.

In general, MPA capped QDs subjected to partial or complete replacement of MPA with MPS produce a higher photoluminescent intensity and quantum yield than QDs synthesized directly with MPA or MPS but maintain the same near infrared emission peak wavelength and absorption edge. Therefore the process of MPS replacement does not change the crystal structure, particle size or unagglomerated and dispersed formation of the nanoparticles. By virtue of the initial precipitation of the QD's from aqueous solution by reaction with MPA, the process enables the formation of QDs having a large particle size, and by virtue of the MPS replacement method, the process enhances QD surface protection, stability and dispersion, while maintaining the large particle size.

Additionally, the QDs have good absorption of excitation energy and a high emission-to-excitation ratio, which may produce high quantum yields. The QDs are also generally able to maintain their PL intensity for more than 60 days under ambient conditions, which is a substantially greater time period than for direct synthesis of MPA or MPS capped QDs whose photoluminescent intensity has been observed to slowly decrease under ambient conditions over time.

3. Biomarker Specific Antibodies

One or more biomarker specific moieties may be selectively conjugated to one or more QDs thereby customizing the QDs to target a desired biomarker. In an exemplary embodiment, one or more selected biomarker specific moieties are specific to one cancer marker. Preferably, the biomarker may be used to determine the presence of a cancer cell. The biomarker may also be used to determine a cancer type, such as invasive carcinoma, and/or malignancy. In an exemplary embodiment, the biomarker is a cancer marker selected from the group consisting of: vascular endothelial growth factor (VEGF), tumor-associated markers such as glycoproteins and carbohydrate antigens (TACAs), such as Tn antigen, T antigen, sial-T antigen, sial-Tn antigen, human epidermal growth factor receptor 2 (HER2) and insulin like growth factor receptor (IGFR). Together, VEGF antigen and Tn-antigen are expressed in about 95% or more of all breast cancer cases and therefore may be highly accurate diagnostic indicators of the presence of breast cancer.

Exemplary biomarker specific moieties that are suitable for detecting VEGF and Tn antigen may include anti-VEGF antibodies and anti-Tn antigen antibodies, respectively. These two types of antibodies are highly selective and have a high expression rate for their respective cancer markers. Preferably, at least one moiety selected from the group consisting of: anti-Tn antigen antibodies and anti-VEGF antigen antibodies, anti-T antigen antibodies, anti-sial-T antigen antibodies, anti-sial-Tn antigen antibodies, anti-HER2 antibodies, and anti-IGFR antibodies are conjugated to the QDs in order to optimize cancer detection sensitivity. In one embodiment, multiple biomarker specific moieties, including different moieties such as anti-VEGF antibodies and anti-Tn antigen antibodies, may be conjugated to a single QD. In another embodiment, one or more biomarker specific moieties may bind two or more QDs to one another.

In an exemplary embodiment, the selected biomarker specific moiety enables the conjugated QDs of the present invention to selectively detect the presence and/or concentration of a biomarker with a high degree of accuracy.

The biomarker specific moieties can be directly bound to one or more reactive groups of the capping agent such as carboxyl, thiol or silanol groups. For example, amino groups found in the biomarker specific moieties can be directly bound to the carboxyl group of MPA. Alternatively, conjugation linkers can be used to bind the biomarker specific moieties to the capping agents of the QDs.

4. Conjugation Linkers

Optionally, one or more conjugation linkers may be used to facilitate the conjugation of one or more biomarker specific moieties to a QD. The conjugation linker may enable conjugation of multiple QDs to a single moiety and/or the conjugation of multiple moieties to a single QD. In one embodiment, two or more conjugation linkers may be used to facilitate conjugation between one or more QDs and one or more biomarker specific moieties, wherein a first conjugation linker may be adapted for binding or have an affinity for the QD and a second conjugation linker is adapted for binding or have an affinity for the biomarker specific moiety to be conjugated.

The conjugation linkers and conjugation schemes may be selected based on the surface chemistry of the QD and the biomarker specific moiety to be conjugated. In one embodiment, a conjugation linker for binding to the QD may include one or more functional groups for reacting and binding with one of the carboxyl, thiol or silanol groups of the capping agent(s) of the QD. Exemplary conjugation linkers may include sulfosuccinimidyl 4-{N-maleimidomethyl]cyclohexane-1-carboxylate (SMCC), succinimidyl-([N-maleimidopropionamido]-n-ethyleneglycol) ester, SM(PEG)$_n$ with n=2,4,6,8,12,24, 1-Ethyl-3-[3-dimethylaminopropyl]carbodiimide hydrochloride (EDC)-N hydroxysulfosuccinimide (NHS), streptavidin (SA) or combinations thereof. The conjugation linker can be used to provide multiple reactive groups per reactive group of the capping agent, or to provide a different reactive group than the reactive group of the capping agent. For example, SMCC reacts with the thiol group of MPS and provides a carboxyl group for reaction with the biomarker specific moiety. SA reacts with the carboxyl group of MPA or SMCC and provides motile biotin binding sites for reaction with biotinylated biomarker specific moieties.

In the case of EDC-NHS, the EDC reacts with a carboxylate group and provides a reactive ester group. The NHS reacts with the ester group and provides a group reactive with amino groups of the biomarker specific moiety.

In certain embodiments, two or more conjugation linkers may be employed. For example, in the case of MPS partial replacement of MPA, it may be desirable to use a first conjugation linker to react with the thiol group of MPS (e.g. SMCC) and a second conjugation linker to react with the carboxyl group of MPA (e.g. SA). Alternatively, it may be desirable to use SMCC to convert all reactive groups of an MPS or MPS-replaced QD to carboxyl groups and then react SA with these carboxyl groups to increase the number of binding sites for biomarker specific moieties.

In an exemplary embodiment, the conjugation linker may have at least about 2 or more, preferably, about 3 or more, more preferably about 4 or more and most preferably, about 5 or more moiety binding sites suitable for binding with the biomarker specific moiety Preferably, an amount of conjugation linker is selected to optimize the binding with the biomarker and/or the photoluminescence intensity of the resultant bound QDs. By selecting appropriate conjugation linkers it is possible to enhance the QD selectivity, sensitivity and/or conjugation efficiency. For example, by binding a larger number of biomarker specific moieties to a particular QD, it is possible to increase the probability of a reaction between the QD and the biomarker in the time period allotted for the reaction. Also, selection of particular conjugation linkers and/or amounts may dictate the size of the resultant conjugated QDs which may influence their binding efficiency.

5. Conjugation Method

The present invention is also directed to a method for conjugating near infrared emitting QDs with one or more biomarker specific moieties. As discussed above, the QDs may be conjugated to a biomarker specific moiety through direct covalent bonding or by using one or more conjugation linkers.

During aqueous synthesis, a conjugation linker is added to and allowed to react with a solution containing capped QDs at a pH of about 7 or less for up to about 45 minutes. If desired, a second conjugation linker may be added to the solution and allowed to react with the QD at about room temperature for about 45 minutes. The resultant product may be centrifuged and/or filtered to remove any unbound conjugation linkers. An additional solution of QDs can optionally be added to bind additional QDs to the conjugated QDs if additional reactive sites are available, for example, when employing SA as the conjugation linker. The conjugation linker is thereby bound to the capping molecules of the newly-introduced QDs by direct covalent bonding. The solution is then allowed to react at about room temperature for about 30 minutes to about 90 minutes and subsequently filtered to remove any unbound QDs.

After one or more conjugation linkers are bound to the QDs, antibodies, such as biotinylated anti-Tn antigen antibodies, biotinylated anti-VEGF antibodies, biotinylated anti-T antigen antibodies, biotinylated anti-sial-T antigen antibodies, biotinylated anti-sial-Tn antigen antibodies, biotinylated anti-HER2 antibodies, biotinylated anti-IGFR antibodies or other antibodies including reactive groups suitable for binding with reactive groups of the conjugation linker, may be bound to the conjugation linker. The moiety: conjugation linked QD molar ratio is preferably optimized for immunofluorescence staining. To conjugate the biotinylated moieties, the biomarker specific moieties may be added to the QD solution and allowed to react for about 30 minutes at about room temperature. The solution may then be filtered to remove any unconjugated moieties.

In another embodiment, a biotin-streptavidin conjugation scheme may be accomplished by using a first conjugation linker having an EDC group and a NHS group, such as EDC-NHS, which reacts with the multiple carboxyl groups on the surface of a QD to form amine-reactive sulfo-NHS esters in the presence of NHS. These amine-reactive NHS esters form a stable amine bond with a second conjugation linker, such as SA, having an affinity for biotinylated antibodies.

In this embodiment, EDC and NHS may be dissolved in a solution including an acid, such as 2-(N-morpholino) ethanesulfonic acid (MES), and a buffer, such as a sodium chloride (NaCl) activated buffer. The QDs are then added into the solution at a pH of about 7 or less, preferably, at a pH less than about 6 and allowed to react for about 15 minutes. 2-mercaptoethanol may then be added to the solution to quench EDC reaction. The second conjugation linker may be subsequently added to the solution and allowed to react with the solution for about 2 hours at about room temperature. The resultant conjugated QD solution may then be filtered.

After the first and second conjugation linkers are bound to the QDs, biotinylated moieties, including biotinlyated anti-Tn antigen, biotinylated anti-VEGF antibodies or other moieties functionalized with biotin, may be bound to the second conjugation linker, which has a strong biotin binding affinity. The moiety:conjugation linked QD molar ratio is preferably optimized for immunofluorescence staining. To conjugate the biotinylated moieties, the biomarker specific moieties may be added to the QD solution and allowed to react for about 30 minutes at about room temperature. The solution may then be filtered to remove any unconjugated moieties.

Using the conjugation method of the present invention, multiple QDs may bind to a single moiety, such as a biotinylated antibody and/or multiple moieties may be conjugated to a single QD when the conjugation linker, such as SA, has multiple moiety binding sites.

6. Method for Cancer Detection

The conjugated QDs may be useful in a wide variety of applications. In particular, they are well suited to determine the presence and/or type of cancer cells in the margins of excised tissue. Therefore, in one embodiment, the invention may be used to immediately determine in real time after surgical excision whether additional tissue removal is required, thereby enabling the surgeon to perform an initial tissue excision and subsequent re-excision in a single surgical procedure. This method may involve the steps of exposing tissue to a solution containing a plurality of biomarker specific moiety conjugated QDs for a sufficient time to allow the QDs to bind to the desired biomarker, removing unbound QDs and determining the presence and/or types of cancer cells based on emission data obtained from exciting the conjugated QD exposed tissue.

First, the QDs of the present invention are conjugated with one or more biomarker specific moieties which are specific to a particular biomarker expressed by the type of cancer being sought. For example, anti-Tn antigen antibodies and/or anti-VEGF antibodies may be conjugated to the QDs when testing for breast cancer.

Upon preparing a solution of the conjugated QDs, a tissue sample excised from a patient may be exposed to the aqueous conjugated QD solution. The tissue sample may be sprayed with, dipped in, covered by, coated with, immersed in or otherwise treated with the conjugated QD solution. The tissue sample may then be incubated for a sufficient period of time to permit the conjugated QDs to locate and bind to any biomarkers present in the tissue. In an exemplary embodiment, the incubation period may be about 30 minutes to about 2 hours. During incubation, the biomarker specific moiety of the conjugated QD will selectively bind to the biomarker expressed by the cancer cell being sought to the exclusion of any other biomarker, thereby avoiding any false positives. Subsequently, the tissue sample may be rinsed with a wash using phosphate buffered saline (PBS) or Tris buffered saline (TBS) with 0.1% Tween to remove any unbound QDs.

The tissue sample is then exposed to excitation light, typically having a wavelength of 300 nm about to about 1100 nm may be employed and more preferably, excitation wavelengths of 350 nm to 800 nm are employed. In response, the conjugated QDs bound to biomarkers located on the surface of and/or embedded within the tissue will fluoresce and emit light in the near infrared range. Using a stereo fluorescence microscope, an observer may reliably determine the presence and location of the biomarkers based on the fluorescence of the QDs. Additionally, a computer or infrared camera may be coupled to the fluorescence microscope to capture and obtain still images or moving images, e.g. video, of the tissue sample being analyzed. Based on the intensity by which the QDs fluoresce, data may be extracted from these images to quantitatively measure the biomarker concentration within the tissue and/or precisely locate the conjugated QDs in the sample tissue. The combination of the tissue penetration depth, lack of interference from auto fluorescence and exceptional brightness of the conjugated QDs enable detection of as few as about 10 to about 100 cancerous cells.

For example, a surgeon upon excising a tumor from a patient may immediately upon removing the tissue examine it to determine the presence or absence of cancer cells in the margins of the excised tissue, in real time. A sample of the excised tissue may be exposed to the conjugated QD solution and evaluated for fluorescence in the operating room or a nearby laboratory. Because little time is required to obtain conclusive results, the surgeon need not close-up the patient while the tissue sample is being examined. If the data obtained from the tissue sample indicates that re-excision is necessary, the surgeon may immediately begin the re-excision procedure without having to schedule a second operation, thereby minimizing healthcare costs, avoiding delays and minimizing risk and pain to the patient. It is envisioned that this method may be particularly useful for the detection of a wide variety of cancers including breast cancer and skin cancer.

EXAMPLES

Example I

Aqueous CdSe QDs conjugated with anti-Tn and antibodies anti-VEGF antibodies were used to image HT-29 colon cancer cells in the margin of excised tissue samples. An aqueous solution of the conjugated QDs was applied to pathological excised tissue sample slides containing tumor masses. The intensity of the photoluminescence was measured to determine if cancer cells were present on the surface of or embedded within the tissue margins.

In this study, breast tissue sections were obtained from multiple patients. Each breast tissue section was divided into three regions: tumor mass, normal surrounding tissue and margin area in which the tissue contained both tumor and normal tissue. Within each region, multiple blocks were cut by pathologists. For each patient sample, two blocks from six margin areas containing tumor mass and normal tissue were examined. The sample tissue blocks were embedded in paraffin, cut to a thickness of about 5 μm and subsequently mounted on glass slides having a positive charge.

To evaluate the effectiveness of the antibody conjugated QDs, the sample slides were stained with the conjugated QDs. This was accomplished by adding the CdSe QDs conjugated with secondary antibodies to the slides and allowing the slides to incubate for about 1 hour. The slides were then washed with tris buffered saline (TBS) about 3 times. The slides were mounted with DAPI for nucleus staining and stored in the dark at about 4° C.

For comparison, the sample slides were also processed using immunohistochemical staining (IHC), the standard pathological evaluation procedure. This was achieved by adding HRP conjugated secondary antibodies (goat anti-mouse) to the slides and incubating for about 30 minutes. The slides were washed with TBS about 3 times. 3,3'-diaminobenzidine DAB was then added to slides and allowed to react for about 10 minutes to develop color. The slides were then washed with PBS and immersed in distilled water for about 5 min.

Hematoxylin and Eosin counter stains were performed for morphological examination. The slides were immersed in Hematoxylin solution for about 2 minutes and then rinsed in tap water for about 3 minutes. The slides were then stained with Eosin for about 2 minutes and dehydrated in ascending concentrations of ethanol of about: 70%, 90% and 100% twice for about 3 minutes each time. The slides were then cleaned with xylene twice for about 3 minutes each time. Finally, the slides were mounted with adhesive chemical permount.

The slides from each tissue block were stained with both QD and IHC to compare the expression pattern between the two types of staining. In one sample, the ex-vivo tissue sample included invasive ductal carcinomas stage III with DCIS low grade mixed. The slides were made from the same block from the posterior margin of the ex-vivo sample. According to pathological report, this block was characterized as having a close margin in which cancer cells were present about 2 mm beneath the surface of the excised tissue.

When compared to the HRP staining, the expression of the markers was similar. Most of the cancer cells showed the expression. Both sections were normalized with the same fluorescent threshold to examine the expression intensity. In the same area of the posterior margin, the expression level of the two markers varied. There were regions where VEGF expression was low compared to that of Tn antigen. The fact that the position of the outermost tumor cells permitted access to blood vessels provides some explanation as to why the VEGF expression seemed to be stronger compared to Tn antigen expression.

Within the same area, the expression of the markers can vary dramatically. For a block in the same posterior margin area as the aforementioned sample tissue block, VEGF was not expressed whereas Tn antigen expression was detected. The same pattern was observed with the HRP staining sections of the same block. A combination of the two markers, however, more accurately detected the presence of cancer cells.

The medial margin of all the tissue samples were evaluated and determined to contain cancer cells in the pathological report. Tn antigen showed strong expression and was an accurate marker for detecting cancer cells.

Figure 1:
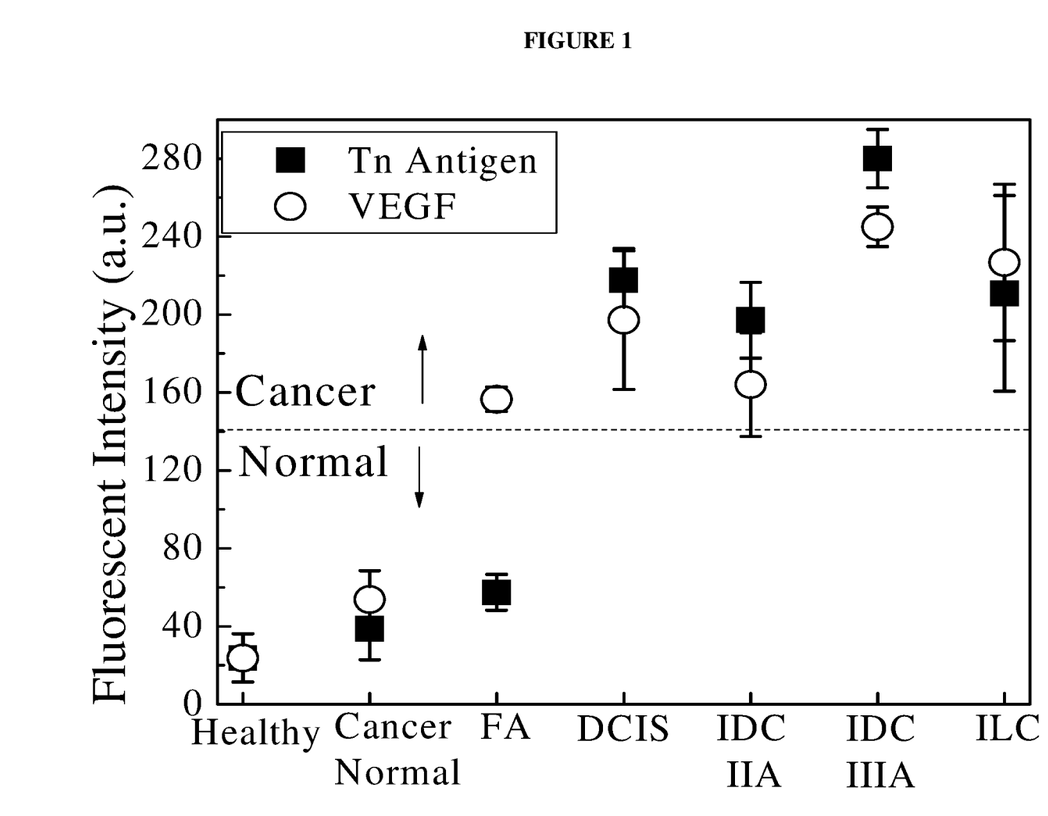
FIG. 1 is a graph of fluorescence intensity per cell for various tissue samples.

The expression of the antibodies was statistically analyzed. Cell counting was performed to determine the percentage of cells showing expression of VEGF and Tn-antigen in the IHC staining and QD staining. To determine expression of markers each block had one control slide to evaluate the background signal. In addition, the normal tissue areas were examined to determine the cut-off threshold of the fluorescence signal. The results of normal region and malignant regions are shown in FIG. 1. The label, "normal," in FIG. 1 refers to tissue blocks from the normal breast tissues of breast cancer patients. The dashed line indicates the threshold intensity for a cell to be identified as a cancer cell based on the statistical analysis set forth in Tables 2 and 3.

TABLE 2

Summary of the average percentage of cancer cells expressing Tn-antigen and VEGF

| Case No. | Stage | VEGF-HRP | VEGF-QD | Tn-HRP | Tn-QD |
|---|---|---|---|---|---|
| 1 | IDC Stage IIA | 76 ± 8.01 | 82 ± 16.4 | 82 ± 14.2 | 94 ± 3 |
| 2 | | 78 ± 19.6 | 85 ± 15.8 | 91 ± 7.9 | 90 ± 4 |
| 3 | | 56 | 85 | 70 | 90 |
| 4 | IDC Stage IIIA | 77 ± 23.8 | 89 ± 4.5 | 86 ± 5.2 | 89 ± 5.3 |
| 5 | | 67 ± 2.3 | 52 ± 26.8 | 94 ± 3 | 93 ± 2.3 |
| 6 | | 72 ± 5.6 | 80 ± 10.2 | 92 ± 1.2 | 91 ± 5.4 |
| 7 | IDC Moderately differentiated - DCIS high grade | 96 | 85 | 90 | 92 |
| 8 | DCIS High Grade | 70 | 60 | 75 | 85 |
| 9 | Fibroadenoma - no carcinoma | 0 | 0 | 0 | 0 |
| 10 | Tubular adenoma, Fibroadenoma, Ductal hyperplasia - no atypia or carcinoma | 78 ± 3.5 | 72 ± 2.8 | 0 | 0 |
| 11 | Invasive Lobular IIIC | 100 | 85 ± 12.4 | 96 ± 2.3 | 96 ± 4.5 |

TABLE 3

Statistics of 47 blocks from 9 cases for both QD and HRP using
VEGF and Tn-antigen as markers

|  | Tn-QD | Tn-HRP | VEGF-QD | VEGF-HRP |
|---|---|---|---|---|
| True positive | 27 | 26 | 25 | 25 |
| False negative | 0 | 1 | 2 | 2 |
| True negative | 38 | 37 | 36 | 36 |
| False positive | 2 | 3 | 4 | 4 |
| Sensitivity | 100% | 96% | 92.5% | 92.5% |
| Specificity | 95% | 92.5% | 90% | 90% |

For both Tn-antigen and VEGF, it was shown that 150 pixels is a good threshold to distinguish whether there is expression. For this study, there were only two benign cases and one healthy case to examine for the cut-off threshold A nucleus size, less than about 3 micron was considered to be a normal cell in the statistical analysis. In most of the cases, the percentage of cells with expression of VEGF and Tn-antigen were consistent between QD and IHC staining. A total of 9 cases (>100 slides) were examined, including 3 IDC Stage II cases, 2 IDC stage III cases, 1 IDC with DCIS high-grade case, 1 DCIS high-grade case and 2 fibroadenoma with no carcinoma cases. Within each case, the percentage of cells with VEGF and Tn-antigen expression varied from slide to slide (i.e., region to region within the tissue). Tn antigen was expressed in all cancer cases although the percentage of cells expressing Tn-antigen varied as noted above. Notably, VEGF is expressed in one fibroadenoma with ductal hyperplasia case. Table 2 shows the average percentage of cells expressing Tn antigen and VEGF in each case.

The percentage of cells expressing of Tn antigen and VEGF are clearly different. In this study, the percentage of cells expressing VEGF for DCIS was about 70% while that of Tn antigen expression was about 85%. In the benign cases, Tn antigen showed no expression; VEGF, however, had some expression in a ductal hyperplasia case. These preliminary results indicate that Tn antigen is an appropriate marker to identify cancer.

Although VEGF showed some expression in the benign cases, it can also be used as an additional cancer marker for breast margin assessment. In the case of fibroadenoma, it's also important to remove the benign tumor completely so that no scar tissue would be formed later that might lead to cancer development. Therefore, it's important to combine these two markers together for margin assessment. In Table 3, we summarize the results of the 47 sample tissue blocks that we analyzed and compare that with HRP. It can be seen that the conjugated QDs performed well in terms of sensitivity and specificity.

Example II

Antibody Conjugated MPS Replaced MPA Capped $Cd_{0.3}Pb_{0.7}S$ Quantum Dots

Figure 2A:
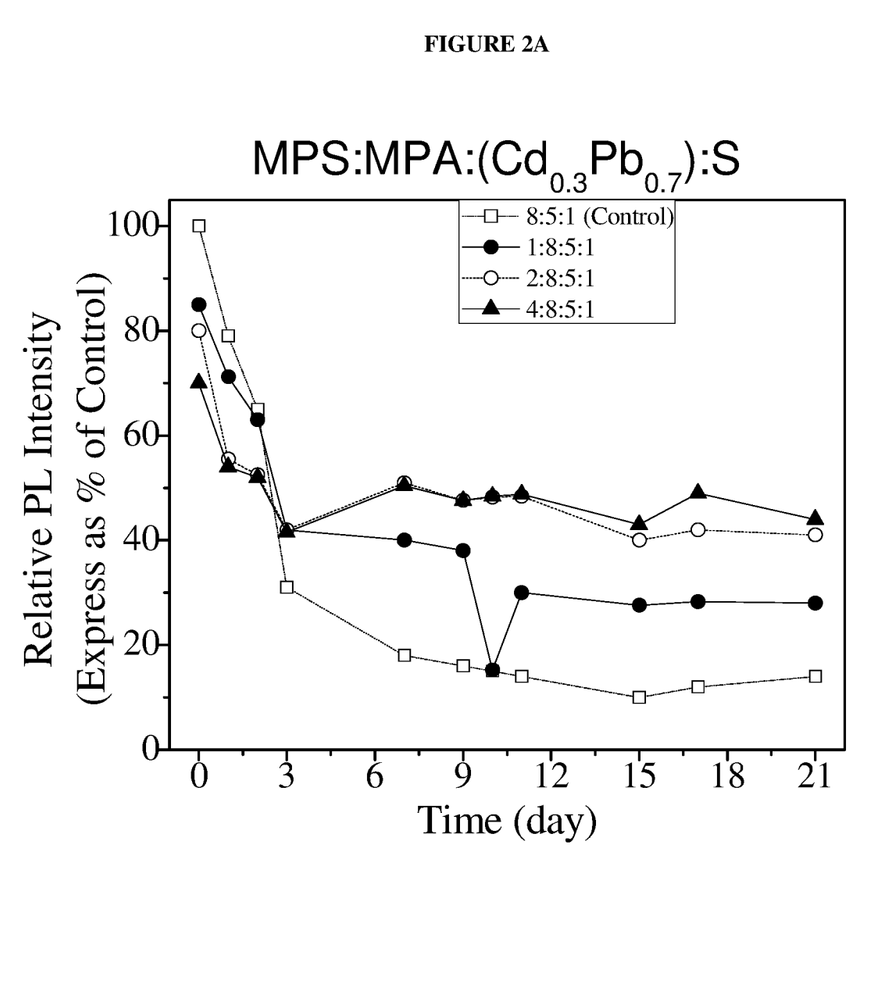
FIGS. 2A and 2B are graphs of relative photoluminescence intensity as a function of time showing CdPbS QD stability with different percentages of MPS replacement of MPA.
Figure 2B:
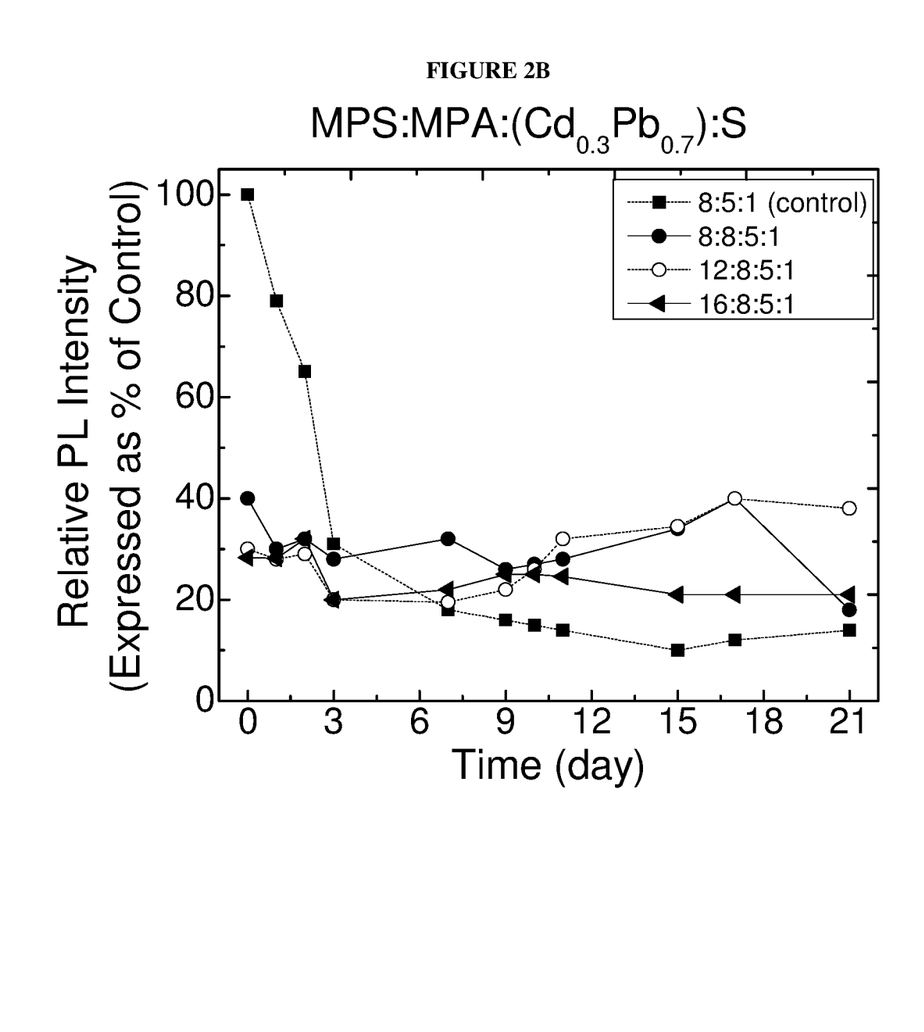

In this study MPS replaced MPA capped $Cd_{0.3}Pb_{0.7}S$ QDs of the present invention were synthesized. To optimize photoluminescent intensity, the CdPbS QD was synthesized to have an MPA:cation:anion molar ratio of about 8:5:1. The synthesized $Cd_{0.3}Pb_{0.7}S$ QD having a 8:5:1 MPA:[excess Cd+$(Cd_{1-x}Pb_x)$]:S molar ratio was stable for a sufficient period of time to enable the detection of cancer cells within the sample excised tissues. To further improve the stability of the QD, some of the MPA capping molecules were replaced with MPS capping molecules. FIG. 2 shows various MPS replaced MPA capped $Cd_{0.3}Pb_{0.7}S$. These QDs were made by reacting a predetermined number of moles of MPS (as indicated by the first of the four numbers) to the 8:5:1 MPA capped $Cd_{0.3}Pb_{0.7}S$ QDs. The MPS replaced QDs were found to remain stable for at least 20 days, maintaining a photoluminescent intensity of at 50% of the initial photoluminescent intensity value.

The resultant synthesized MPS replaced MPA capped CdPbS QDs were unagglomerated, had a particle size of about 3 nm, were stable for at least 20 days and generated a near infrared emission in the range of about 800 nm to about 950 nm.

MPS replaced MPA capped CdPbS QDs having a broader near-infrared emission range were also synthesized. In general, cadmium sulfide bulk has a band gap of about 2.4 eV, corresponding to a wavelength of about 517 nm. By contrast, PbS bulk has a band gap of about 0.37 eV, corresponding to a wavelength of about 3351 nm.

Example III

Cancer Detection Study Using Biotinylated Antibody Conjugated to MPS Replaced MPA Capped CdSe QDs Using SMCC and SA Biotinylated antibodies were conjugated to MPS replaced MPA capped CdSe QDs having an 8:5:1 molar ratio of MPA:Cd:Se using the conjugation linkers, sulfosuccinimidyl 4-[N-maleimidomethyl]cyclohexane-1-carboxylate (SMCC) and streptavidin (SA) to form a biotin-streptavidin conjugation scheme. The conjugated QDs were used to detect the presence of cancer cells within the margins of breast tissue excised from breast cancer patients.

SMCC and SA were used to bind biotinylated antibodies to the MPS replaced MPA capped CdSe QDs in a biotin-streptavidin conjugation scheme. SMCC was bound to MPS replaced MPA capped CdPbS QDs and was also bound to SA, which in turn was bound to a biotinylated antibody. SMCC was allowed to react with the QD at a pH of about 7 for an initial period of about 45 minutes at about room temperature. Excess SMCC was then removed from the solution by size exclusion. The NHS ester end of SMCC was also allowed to react with the primary amines of the SA structure at a pH of about 7. The unbound QDs and SA were subsequently removed by micro-centrifugation using a 100 KDa filter.

Figure 3:
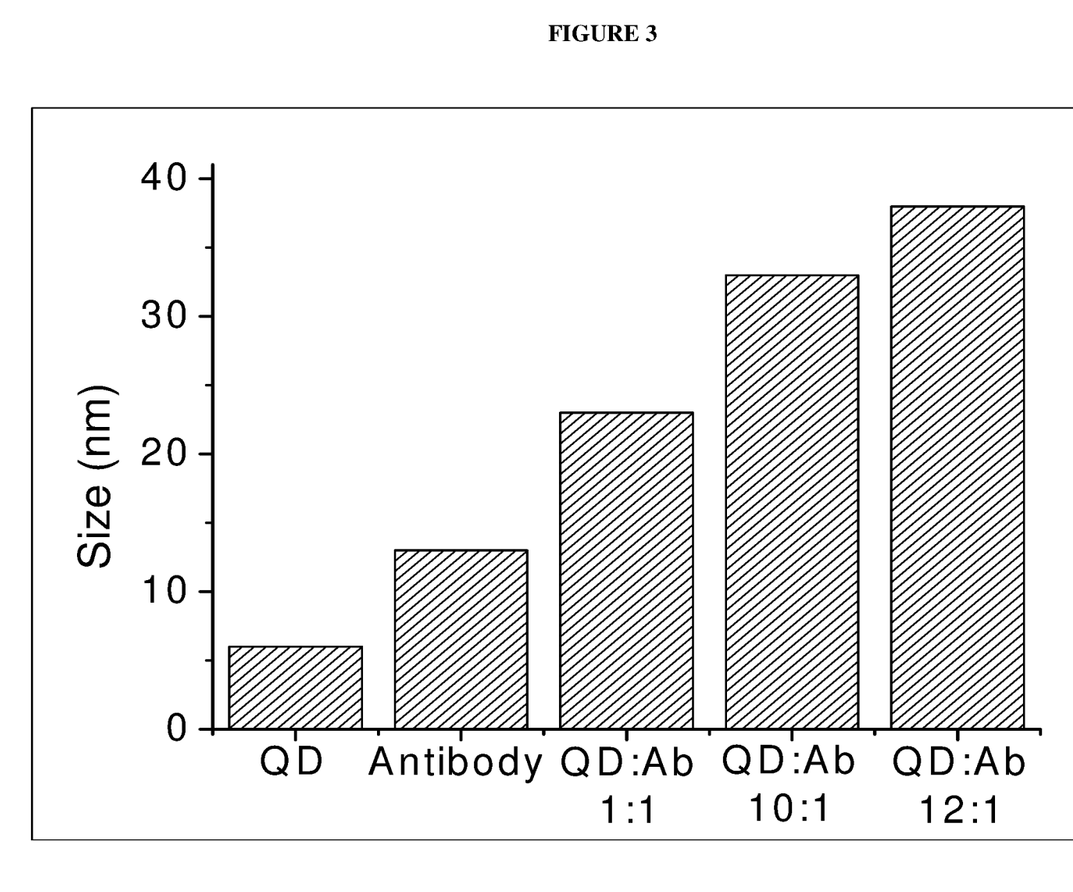
FIG. 3 shows the particle sizes of antibody conjugated QDs wherein different molar ratios of QDs were conjugated with the antibody thereby demonstrating that multiple moles of QDs can be conjugated to a single mole of antibody.

A QD: SA molar ratio was selected to optimize coverage of SA on the surface of the QDs. During synthesis, SMCC was first mixed with TRITC tagged SA in a 40:1 SMCC:SA molar ratio. The concentration of SA was about 200 µg/mL. The mixture was allowed to react at about room temperature for about 45 min. Samples of the mixture were then centrifuged using a 10K micro-filter to filter out any unbound SMCC. CdSe QD solution was then added to the samples in an amount to achieve a QD:SA molar ratio of about 5:1, about 6:1, and about 10:1. The reaction took place at about room temperature for about 60 minutes. Each sample was then filtered using a 100K micro-filter to remove any unbound QDs. The solution was then dropped onto the positively charged surface of a glass slide allowing the QDs to be captured and bound to the slide by electrostatic binding. Images of the QDs were taken using MicroVista CCD camera. The results are shown in FIG. 3.

To examine the effectiveness of the conjugation, we used cy3 which emitted red light to tag streptavidin. The QDs used in this study emitted green light. After the conjugation steps, we then deposit the cy3-strepavidin/QDs mixture on a positively charge glass slide. After washing, unbound streptavidin which was slightly positively charged was washed away. Only the negatively charged QDs and QD-streptavidin complex remained on the glass slide surface. The presence of green color fluorescence indicates unbound QDs while yellow color fluorescence indicates QDs conjugated with steptavidin. The results showed that a 10:1 QD:SA molar ratio produced the strongest overlap of the green and the red fluorescence on the positive glass slides, yielding the most yellow signal uniformly distributed throughout the glass slide. The percentage of QDs that were conjugated to streptavidin was estimated as the ratio of the total intensity (intensity multiplied by area) of the yellow to the total intensity of both the yellow and the green. Using this criterion, we estimated about 90% of the QDs with the 10:1 QD:SA molar ratio were conjugated. Only about 10% of the QDs with a 5:1 and 6:1 QD:SA molar ratio were conjugated to streptavidin. In addition, more aggregations were observed in the other ratios than 10:1. SMCC was found to link more QDs together than SA. QDs having an SA:QD molar ratio of about 10:1 were the most effective in binding SA to the QDs.

After SA was successfully bound to the QDs, biotinylated antibodies (Ab) were bound to the SA-QD via a biotin-streptavidin binding mechanism in a molar ratio of 1:12 Ab:SA-QD. The molar ratio was optimized for the best immunofluorescence staining signal. Anti-VEGF and anti-Tn antigen, which are specific to breast cancer markers, were the selected antibodies. The selected antibodies were found to have substantially greater expression levels than IGFR antibodies.

To conjugate the biotinylated antibody to the SA-QD, an appropriate amount of antibody (Ab) was added to the SA-QD solution, and the mixture was allowed to react for about 30 minutes at about room temperature. Unconjugated antibodies were removed from the mixture by a size exclusion filter. The size of the resultant Ab conjugated SA-QDs were measured using a nanosizer. A SDS-PAGE gel was also performed to validate the conjugation.

From these results it was determined that as the Ab:SA-QD molar ratio increased, the particle's size also increased. Immunofluorescent staining on HT29 cell was performed to further confirm the results.

To investigate the effectiveness of the anti-VEGF and anti-Tn biotinylated antibody conjugated QDs, the QDs were used to detect colon cancer HT29 and activated fibroblast NIH 3T3 cancer cells contained within tissue specimens. HT29 cells, which express Tn antigen strongly, were purchased from ATCC. NIH 3T3 fibroblasts were activated with fetal bovine serum (FBS) to mimic the cancer adjacent cells. VEGF is over-expressed in NIH 3T3 but not Tn antigen. NIH 3T3 cells were used for VEGF expression, and HT29 cells were used to express Tn antigen.

To prepare the tissue samples, HT29 and NIH 3T3 cells were cultured in McCoy medium and DMEM respectively with about 10% FBS and about 1% Penn/Strep. After reaching 80% confluent on chamber slides, the cells were fixed with 4% paraformaldehyde for about 15 min. Cells were then blocked with streptavidin, biotin, and about 3% hydroperoxide for about 15 minutes during each step and about 10% goat serum for about 1 hour at about room temperature. Mouse anti-VEGF IgG and mouse anti-Tn antigen IgM were incubated on the slides for about 1 hour at a concentration of about 1:100 and 1:75 respectively. The samples were then washed with about 1% Tween TBS buffer. The slides were incubated with about 200 µL QD conjugated with secondary goat anti-mouse for about 30 minutes at about room temperature. Finally, the slides were washed with TBS and counter-stained with DAPI.

For Tn antigen, NIH 3T3 was used as negative control since the cells do not express Tn antigen. For specificity of the antibodies, control samples were not incubated with primary antibodies but only the QD labeled antibodies. In addition, the positive control with Cy3 labeled secondary antibody was used to observe the expression patterns of VEGF and Tn antigen.

Using the optimal conjugation condition, VEGF and Tn antigen were visualized using immunofluorescent staining. It was expected that the expression of these biomarkers would be on the cellular membranes. The control samples did not exhibit any fluorescent signal, thereby supporting the detection specificity of the anti-VEGF and anti-Tn antibodies. Both the cy3 labeled and QD labeled antibodies showed similar expression pattern, which suggests that the QD detection method was comparable to commercial fluorescent probes in terms of specificity. The QD labeled antibodies, however, exhibited stronger fluorescent signal and therefore enhanced detection sensitivity than the cy3 labeled antibodies.

To further investigate the specificity of the conjugated QDs, the conjugated QDs were used to detect the presence of cancer cells in lymphocyte tissue specimens containing different amounts of NH3T3 and HT29 cells, wherein the NH3T3 and HT29 cell lines were stained together. The NIH 3T3 and HT29 cells were cultured until about 80% confluent. The cells were then trysinized and spun down into cell blocks. The cells blocks were frozen in liquid nitrogen for about one hour. OCT molds were prepared with NIH 3T3 and HT29 blocks placed next each other on dry ice. The frozen blocks were then sectioned at 5 µm and stained with the same protocol described previously.

A MicroVista NIR CCD camera connected to an optical microscope was used to capture visible and NIR images of the tissue samples. Tn antigen was detected using the indirect immunofluorescent staining with QD labeled antibodies. The conjugated QDs were specific to the marker when both cell types were stained together. NIH 3T3 did not show any fluorescent signal compared to HT29 cells.

Example IV

Cancer Detection Study Using Biotinylated Antibody Conjugated to MPA Capped CdSe QDs Using EDC-NHS and SA Biotinylated antibodies were conjugated to MPA capped CdSe QDs using 1-Ethyl-3-[3-dimethylaminopropyl]carbodiimide hydrochloride (EDC)-N hydroxysulfosuccinimide (NHS) and streptavidin (SA) in a biotin-streptavidin conjugation scheme. The QDs were used to detect the presence of cancer cells within the margins of breast tissue excised from breast cancer patients.

EDC-NHS and SA were used to bind biotinylated antibodies to the MPA capped CdSe QDs in a biotin-streptavidin conjugation scheme. The surface of MPA capped CdSe QDs has multiple carboxyl groups due to its capping molecules. The EDC reacted with these carboxyl groups to form amine-reactive sulfo-NHS esters in the presence of NHS. The amine-reactive NHS ester then form a stable amine bond with streptavidin.

During synthesis, about 4 mM of EDC and about 5 mM of NHS were first dissolved in about 0.1 M MES, activated buffer. Then about 0.8 mM of QDs was added into the solution at a pH of about 6. The reaction was allowed to occur for about 15 min. About 20 mM of 2-mercaptoethanol was then added into the solution to quench the EDC reaction. Excess EDC and 2-mercaptoethanol were filtered with a 10 kDa microscentrifuged filter. Streptavidin was finally added to the solution and reaction took place for about 2 hours at about room temperature. The resultant solution containing streptavidin conjugated NHS-EDC was then filtered with a 100 kDa microcentrifuged filter.

The SA conjugated EDC-NHS QD was then conjugated with biotinylated anti-VEGF antibodies and anti-Tn antigen antibodies via a biontin-streptavidin binding mechanism in the same manner as previous describe in Example III. The Ab:SA conjugated QDs molar ratio was about 1:3.

To investigate the effectiveness of the anti-VEGF and anti-Tn biotinylated antibody conjugated QDs, the QDs were used to detect colon cancer HT29 and activated fibroblast NIH 3T3 cancer cells contained within tissue specimens in the same manner as taught by Example III.

Using the optimal conjugation conditions, VEGF and Tn antigen were visualized using immunofluorescent staining. It was expected that the expression of these biomarkers would be on the cellular membranes. The control samples did not exhibit any fluorescent signal, thereby supporting the detection specificity of the anti-VEGF and anti-Tn antibodies. Both the cy3 labeled and QD labeled antibodies showed similar expression patterns, which suggests that the QD detection method was comparable to commercial fluorescent probes in terms of specificity. The QD labeled antibodies, however, exhibited stronger fluorescent signal and therefore enhanced detection sensitivity relative to the cy3 labeled antibodies.

When different amounts of NH3T3 and HT29 cells in lymphocyte tissue specimens were stained together, Tn antigen was detected using indirect immunofluorescent staining with QD labeled antibodies. The conjugated QDs were specific to the marker when both cell types were stained together. NIH 3T3 did not show any fluorescence signal compared to HT29 cells.

In comparing the biotinylated antibody conjugated MPA capped CdSe QDs of the present example and Examples III, the QDs that were conjugated using the SMCC conjugation linker required a higher concentration of QDs to obtain a strong fluorescence signal in comparison to the QDs that were conjugated using the EDC-NHS conjugation linker.

The foregoing examples were presented for the purpose of illustration and description only and are not to be construed as limiting the invention in any way. The scope of the invention is to be determined from the claims appended hereto.

Example V

Study Using Biotinylated Antibody Conjugated to MPA Capped QDs Using SMCC

In this study, QDs are directly conjugated to antibody (Ab) using SMCC as the bifunctional linker using the method described in Example 3 using the anti-Tn antigen antibody except that no streptavidin was employed in this example. After conjugation, the conjugated QD-Ab complex was purified by filtering out unbound antibody and unbound QDs by microcentrifugation with a 200 kDa filter. The retentate, which contained only the QD-Ab complexes, and the filtrate, which contained both the unbound QDs and unbound Abs, were passed through channels of a SDS-PAGE electrophoresis gel to examine the quantity and the size of the QD-Ab complex. Bright-filed and fluorescent images of a gel containing the free antibody and 3 gels containing QD-Ab complex of different molar ratios, namely a QD:Ab ratio 1:1, 10:1, and 12:1 were obtained. The QDs used in this study had an orange color. The free antibody showed up in the bright field of the gel containing the free antibody but not in the fluorescent mode. Furthermore, Ab showed up at a band of about 100 kD and another band of about 35 kD. The less than 165 kD size of the Ab was presumably due the cleavage of the Ab by the electrophoresis process. In comparing the results of the 3 QD-Ab complex gels to the free Ab gel, one can see that the QD-Ab complexes had the same molecular size as the free Ab indicating the QD-Ab complexes contained only one Ab. Furthermore, the QD-Ab complexes showed fluorescence indicating that the Abs were conjugated to QDs.

To quantify the number of QDs bound to each Ab, we carried out the gel electrophoresis experiment for the free QDs and the free Abs alone at various concentrations. Using ImageJ, the area and the intensity of Ab bands were measured. An integrated intensity was then obtained for each Ab concentration to construct a standard curve for the Ab. Using a similar approach, a standard curve was also obtained for the QDs. From the standard curves, the amount of unbound Abs and unbound QDs were determined as well as the bound ones. Once the total number of QDs and that of the Abs in the Ab-QD complex bands were determined. The number of QD bound to each Ab was then determined by dividing the number QDs by the number of bound antibodies. The result of the analysis indicated that the QD-Ab complexes with a QD:Ab=1:1 consisted of 1Ab bound with 1QD. The complexes with QD:Ab=10:1 consisted of 1Ab bound with 3QDs whereas complexes with QD:Ab=12:1 consisted of 1Ab bound with 4-5 QDs.

Example VI

The procedure of Example I was repeated for VEGF quantum dots and Tn quantum dots for a larger patient population and the results are given in Table 4 below.

TABLE 4

Comparison of Sensitivity and Specificity of Tn-antigen and VEGF using IF and IHC staining. (a) statistics based on 126 cases; (b) statistics based on 410 blocks.

|  | VEGF-QD | Tn-QD |
| --- | --- | --- |
| (a) 126 Cases |  |  |
| True Positive | 54 | 60 |
| False Negative | 12 | 6 |
| True Negative | 44 | 54 |
| False Positive | 16 | 6 |
| Sensitivity | 93% | 94% |
| Specificity | 78% | 92% |
| (b) 410 Blocks |  |  |
| True Positive | 179 | 183 |
| False Negative | 19 | 15 |
| True Negative | 185 | 213 |
| False Positive | 61 | 33 |
| Sensitivity | 94% | 94% |
| Specificity | 77% | 88% |

The foregoing examples have been presented for the purpose of illustration and description and are not to be construed as limiting the scope of the invention in any way. The scope of the invention is to be determined from the claims appended hereto.

What is claimed is:

1. A method for conjugating one or more biomarker specific moieties to one or more quantum dots comprising the steps of:
   a) reacting a conjugation linker with an aqueous solution containing the quantum dots capped with at least one thiol-functionalized capping agent to form a reaction product,
   wherein said quantum dots have a core selected from the group consisting of metal sulfide and metal selenide, the core includes one or more different metals which are capped with a mercaptocarboxylic acid capping agent, part of said thiol-functionalized capping agent is replaced with mercaptosilane capping agent to provide both a molar ratio of moles of mercaptosilane capping agent to moles of quantum dots of from about 0.2:1 to about 8:1, and a molar ratio of the capping agents: metal:Se or S is from about 2:1:1 to about 16:8:1;
   b) removing any unbound conjugation linkers from the reaction product of step a); and
   c) reacting the mixture of step b) with the one or more biomarker specific moieties.

2. The method of claim 1, wherein said thiol-functionalized capping agent is selected from the group consisting of: 4-aminothiophenol and mercaptocarboxylic acids.

3. The method of claim 1, wherein the conjugation linker has a binding affinity for biotin and wherein the one or more biomarker specific moieties is functionalized with biotin.

4. The method of claim 1, wherein the one or more biomarker specific moieties is conjugated to the quantum dot using a biotin-streptavidin conjugation scheme.

5. The method of claim 1, wherein the conjugated quantum dots have a core that is linked to the biomarker specific moiety through a mercaptosilane capping agent.

6. The method of claim 5, wherein the mercaptosilane capping agent comprises 3-mercaptopropyltrimethoxysilane.

7. The method of claim 5, wherein the core is selected from the group consisting of CdSe, CdPbS, and ZnSnS.

8. The method of claim 7, wherein the molar ratio of the capping agents:metal:Se or S is from about 4:3:1 to about 8:5:1.

9. The method of claim 5, wherein the core comprises two different metals.

10. The method of claim 1, wherein the conjugation linker is a mercaptosilane capping agent.

11. The method of claim 10, wherein the mercaptosilane capping agent is 3-mercaptopropyltrimethoxysilane.

12. The method of claim 1, wherein the conjugation linker is selected from the group consisting of sulfosuccinimidyl 4-[N-maleimidomethyl]cyclohexane-1-carboxylate,succinimidyl-([N-maleimidopropionamido]-n-ethyleneglycol) ester, SM(PEG)n with n=2,4,6,8,12,24, 1-Ethyl-3[3-dimethylaminopropyl]carbodiimide hydrochloride-N hydroxysulfosuccinimide and streptavidin.

13. The method of claim 1, wherein the conjugation linker comprises two different conjugation linkers.

14. The method of claim 1, wherein the at least one thiol-functionalized capping agent is a mercaptocarboxylic acid.

15. The method of claim 14, wherein the mercaptocarboxylic acid capping agent is selected from the group consisting of mercaptoacetic acid, mercaptopropionic acid, mercaptosuccinic acid, mercaptobenzoic acid, and mercaptoundecanoic acid.

16. The method of claim 1, wherein the biomarker specific moiety is selected from the group consisting of anti-VEGF antibody, anti-Tn antigen antibody, anti-T antigen antibodies, anti-sial-T antigen antibodies, anti-sial-Tn antigen antibodies, anti-HER2 antibodies and anti-IGFR antibodies.

17. The method of claim 1, wherein the molar ratio of the conjugation linker to the quantum dots is from about 0.5 to about 4.

* * * * *